United States Patent [19]
Bryant

[11] Patent Number: 5,431,280
[45] Date of Patent: Jul. 11, 1995

[54] CLOSURE CAP FOR HOLDING PIPETS DURING SHIPPING

[75] Inventor: Debra L. Bryant, Charlottesville, Va.

[73] Assignee: Humagen Fertility Diagnostics Inc., Charlottesville, Va.

[21] Appl. No.: 214,806

[22] Filed: Mar. 17, 1994

[51] Int. Cl.⁶ .................. B65D 51/16; A61B 10/00
[52] U.S. Cl. ........................ 206/363; 128/763; 215/307; 604/256
[58] Field of Search ............... 604/256; 206/363, 364, 206/365, 367; 215/307, 355; 128/760, 763

[56] References Cited

U.S. PATENT DOCUMENTS

| | | | |
|---|---|---|---|
| 1,592,462 | 4/1926 | MacGregor | 206/365 X |
| 3,637,072 | 1/1972 | Narusawa et al. | 206/365 X |
| 3,948,261 | 4/1976 | Steiner | 206/367 X |
| 4,237,883 | 12/1980 | Akhavi | 206/365 X |
| 4,576,595 | 3/1986 | Aas et al. | |
| 4,777,964 | 10/1988 | Briggs et al. | |
| 4,786,281 | 11/1988 | Valentini et al. | |
| 4,893,636 | 1/1990 | Cook et al. | |
| 4,979,515 | 12/1990 | Briggs et al. | |
| 5,060,659 | 10/1991 | Cook et al. | |
| 5,131,404 | 7/1992 | Neeley et al. | |
| 5,188,607 | 2/1993 | Will | |
| 5,203,825 | 4/1993 | Haynes et al. | |
| 5,325,977 | 7/1994 | Haynes et al. | 215/307 |

Primary Examiner—Bryon P. Gehman
Attorney, Agent, or Firm—Sheldon H. Parker

[57] ABSTRACT

A closure cap for protecting a capillary tube incorporates a hollow body member is dimensioned to fit within a container. The container and closure cap are used in shipping micropipets in a impact absorbing, sterile environment. An elongated tube retaining portion is centrally positioned within the hollow body member and extends at least a substantial portion of the length of the body. The tube retaining portion has a centrally disposed channel with at least one open end for receiving and retaining a tube in a friction fit. The air tight seal allows for sterility. A plurality of radially extending, equally spaced, retaining webs connect the tube retaining portion and the body along at least a major portion of the length of the tube retaining portion. The closure cap is air impermeable, flexible and formed of an inert material which is heat and radiation resistant.

29 Claims, 2 Drawing Sheets

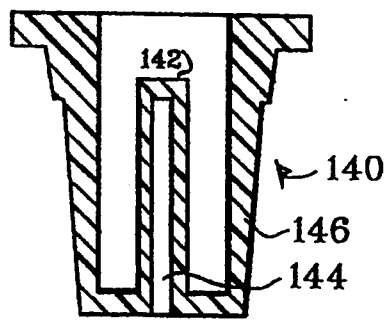
FIG.4
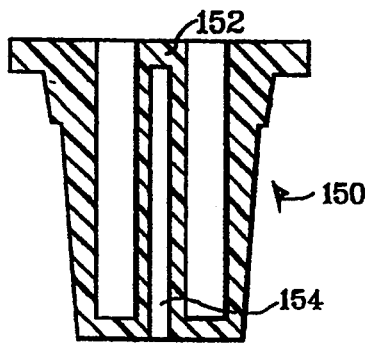
FIG.5
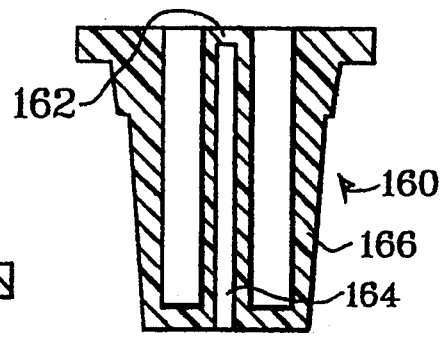
FIG.6
FIG.8
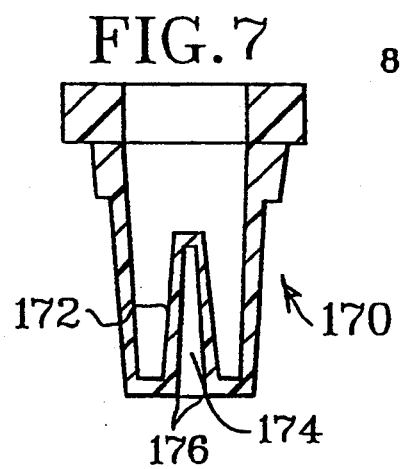
FIG.7
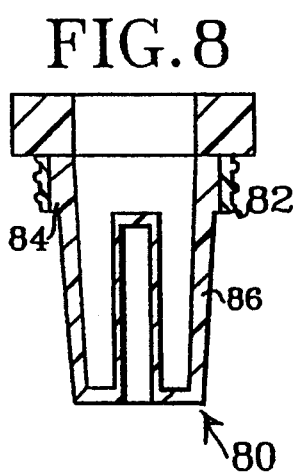
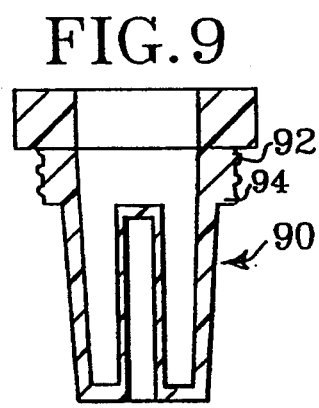
FIG.9

CLOSURE CAP FOR HOLDING PIPETS DURING SHIPPING

BACKGROUND OF THE INVENTION

1. Field of the Invention

The instant invention discloses a novel device to store and ship sterile micropipets without the breakage presently incurred. The disclosed closure cap maintains the micropipet suspended within the shipping tube and prevents breakage due to the swinging of the micropipet during movement.

2. Brief Description of the Prior Art

Micropipets, or capillary tubes, are frequently used to gather, measure and/or transport various types of liquid specimens, such as blood and sperm, as well as chemical solutions and suspensions. Micropipets are small, thin glass tubes designed for drawing liquid by means of capillary action, or applied suction, and retaining such liquid through surface tension, adhesion or applied suction. Micropipets handle small quantities of liquids, up to 1 ml, while the standard pipets will range in capacity from 1.0 to 50.0 ml. The delicate construction of the pipets requires extreme caution in handling and shipping. For many biological specimens the pipets are required to be sterile and it is preferable that the pipets be shipped in a sterile atmosphere ready for use rather than requiring sterilization just prior to use.

Commercially available stoppers for test tubes are made from a flexible, inert material. The body portion of the stopper is provided with a receiving passage dimensioned to received the outer diameter of the pipet being sealed. U.S. Pat. No. 4,576,595 to Aas discloses an improvement over the prior art for anaerobically sealing a capillary tube containing a liquid sample. The '595 patent solves a problem of air expulsion by venting to the atmosphere the inner space of the stopper while the open tube end is inserted into a skirt portion.

Cook et al discloses a stopper for use in containers for blood collection in U.S. Pat. No. 4,893,636 and 5,060,659. The stopper is particularly designed for use with relatively small size blood collection tubes and enables these tubes to be used with tube holders sized for use with larger collection tubes. The stopper is provided with a diaphragm portion which allows insertion of a collection tube from the collection device to the smaller tube.

U.S. Pat. No. 5,203,825, issued to Haynes et al, discloses a Capillary Tube Assembly Including A Vented Cap which allows a liquid to be drawn into the capillary tube. U.S. Pat. No. 5,188,607 and U.S. Pat. No. 4,786,281 both deal with valve connectors for use with syringes, etc.

Although the foregoing prior art discloses caps for tubes used in the collection and transference of specimens, none address the problem of sterility. Additionally, none of the caps disclosed above are designed for safe shipment of the pipets.

A method for shipping blood sampling glass vials is disclosed in U.S. Pat. No. 4,777,964 and U.S. Pat. No. 4,979,515 to Briggs et al. The '964 patent discloses a home use AIDs sample gathering kit, wherein the user gathers the blood sample in the provided glass vials, seals the vials with a putty substance and mails the vials to a testing facility using the provided cardboard base member 12. The Briggs patents do not address the issue of sterility as neither the vials nor the shipping container would be able to remain sterile after home use. The vials used in the Briggs patent must be manufactured of heavier weight glass, thereby forming a thicker wall, than pipets due to the minimum amount of protection provided by the lightly padded cardboard base.

U.S. Pat. No. 5,131,404 discloses a transportation device which is constructed to handle capillary tubes. The capillary tube carrier tube 1 has a closure cap 3 and an internal divider 5 which subdivides the interior of the tube 1 into cells for receiving the capillary tubes 7 after the samples have been drawn. A pad 8 is positioned in the bottom of the tube 1 for cushioning the bottoms of the capillary tubes 7. The cap 3 has a layer of closure putty 18 adhered to the inside of the top end thereof for use in plugging an end of capillary tubes placed therein after specimen samples have been drawn into the capillary tubes. A shoulder 19 is formed on the interior side wall of the cap 3 for engaging the top surface of the carrier tube 1 to limit the extent of telescoping of the cap 2 over the tube 1. This ensures that a gap will be preserved between the top ends of the capillary tubes 7 in the tube 1 and the putty layer 18 in the cap 3. The device of the '404 patent places four capillary tubes within the same carrier tube and places them vertically within a carrier. This method, although providing sufficient protection for carrying, would not provide sufficient protection for shipping. Additionally, to maintain sterility, shipment from the manufacturer should only be a single pipet per shipping container. Once a shipping container is opened, the sterility is lost and the remaining pipets would be contaminated.

The prior art is replete with caps for use with test tubes and capillary tubes. None of the prior art, however, has addressed the problem of safely shipping sterile pipets. Safe shipment of delicate pipets cannot easily and reliably be accomplished by combining a prior test tube cap and a vial. The instant invention overcomes the problems of the prior art by disclosing a closure cap which retains the pipet safely within a shipping tube, allowing for safe, sterile transportation.

BRIEF DESCRIPTION OF THE DRAWINGS

The advantages of the instant disclosure will become more apparent when read with the specification and the drawings, wherein:

FIG. 4 is a cutaway side view of an unsuccessful test cap;

FIG. 5 is a cutaway side view of an additional unsuccessful test cap;

FIG. 6 is a cut away side view of a further unsuccessful test cap; and

FIG. 7 is a cut away side view of an alternate embodiment of the instant invention.

FIG. 8 is a cut away side view of an alternate embodiment of the instant invention for used with a threaded container; and FIG. 9 is a cut away side view of an alternate embodiment to FIG. 8.

SUMMARY OF THE INVENTION

Figure 1:
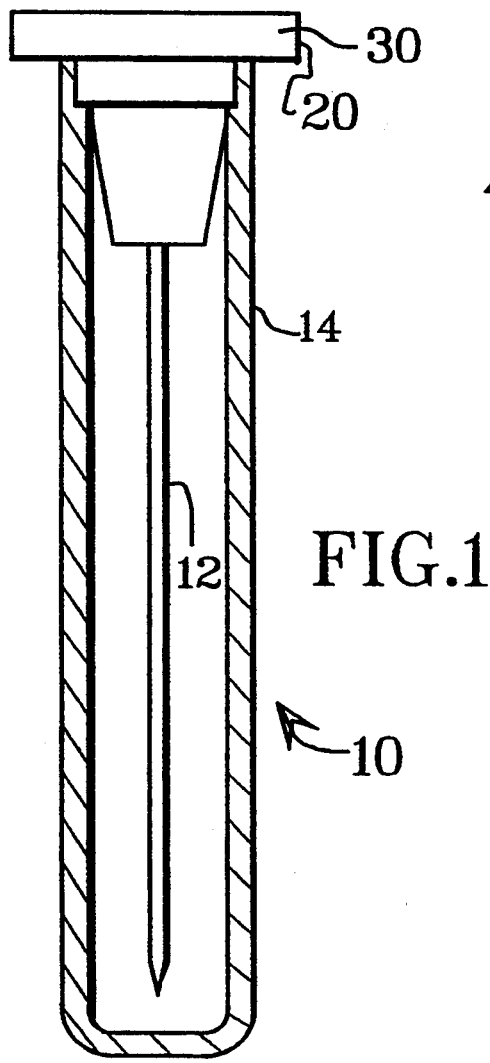
FIG. 1 is a side view of the closure cap of the instant invention holding a pipet within the shipping tube.

A closure cap for use in protecting a capillary tube, or the like, has a hollow body member with a first end and a second end and an exterior wall dimensioned to fit within a container. The container and closure cap is used in shipping micropipets in a impact absorbing, sterile environment. A tube retaining portion is an elongated member substantially centrally positioned within the hollow body member and extends at least a substantial portion of the length of the hollow body member. The tube retaining portion has a centrally disposed channel with at least one open end for receiving and retaining a tube, such as a micropipet, in a friction fit. An air tight seal, formed by an air sealing area in combination with the sealing region, is provided thereby preventing air from entering or exiting the container.

A plurality of radially extending, equally spaced, retaining webs connect the tube retaining portion and the exterior wall and line in a plane which is parallel to the axis of the tube retaining portion. The webs radiate outwardly from the tube retaining portion to the body member and connect the tube retaining portion and the body member along at least a major portion of the length of the tube retaining portion. The webs have sufficient rigidity to provide structural rigidity to at least a portion of the closure cap exterior wall. A sealing region, positioned between the first end and the second end, has a periphery slightly greater than that of the region of the exterior wall between the sealing region and the first end. A gripping portion has an outer periphery greater than the outer periphery of the sealing region and is positioned between the sealing region and the second end. The hollow body member is tapered inwardly from the sealing region to the first end, with a cylindrical region proximate the second end and a conical region proximate the first end. The conical region allows for ease of insert of the closure cap into the shipping member. The body member and the tube retaining portion are substantially coaxial. The closure cap is air impermeable, flexible and formed of an insert material which is heat and radiation resistant.

DETAILED DESCRIPTION OF THE INVENTION

The instant closure cap 20 is specifically designed to protect the end of the micropipet from breakage, both in shipping and in use. Many pipets are not used to ship specimens but rather to move a specimen from one location to another within a lab or hospital, particularly when micropipets are used in fertilization. The ends of the micropipet have been manufactured to perform various tasks in the IVF lab and due to their fine, delicate construction, require extreme protection. In some pipets, one end is rounded and used with suction to hold an egg. Other pipets resemble needles under the microscope and are used to pick up single sperm and insert them into the egg. The insertion of the sperm into the egg is the most sophisticated form of in vitro fertilization. The tip of the micropipet must be protected from time of manufacture to time of disposal. The closure cap 20 construction allows for the protection of the tip from time of insertion into the cap to time of removal.

The closure cap 20, in conjunction with the shipping tube 14, can also be used to ship specimens from location to location. A standard capillary tube can easily be substituted for the micropipet described herein. The capillary tube can be delivered to the testing site in the tube and replaced in the shipping tube, with the sample, for delivery to a lab. This is particularly of interest in outlying regions where samples must be transported over distances to the testing facility.

FIG. 1 illustrates the assembled shipping unit 10 which comprises the closure cap 20, micropipet 12 and shipping tube 14. The shipping tube 14 is preferably a standard tube of the type used for sample specimen collection, which provides an inexpensive, easily sterilized unit for shipping. The micropipet 12 is a standard glass micropipet which is used for collection of and transfer specimen samples. Within the instant disclosure, reference will be made to the needs of biological specimens, however the micropipet 12 can also be used for transportation of non-biological samples. The closure cap 20 provides the integral piece in protecting the micropipet 12 from breakage during shipping. The closure cap 20 illustrated herein is designed to fit a 12×75 mm shipping tube, such as a Falcon #2025 polystyrene tube. The closure cap is sized to hold a 1 mm O.D. micropipet, however other size pipets can be use by modifying the dimensions. The dimensions used herein are used as a reference and are not intended to limit the scope of the disclosure. It will be obvious to one skilled in the art that the dimensions can easily be altered to fit other size tubes and/or micropipets, or that the micropipets can be replaced with other types of cylinders.

Figure 3:
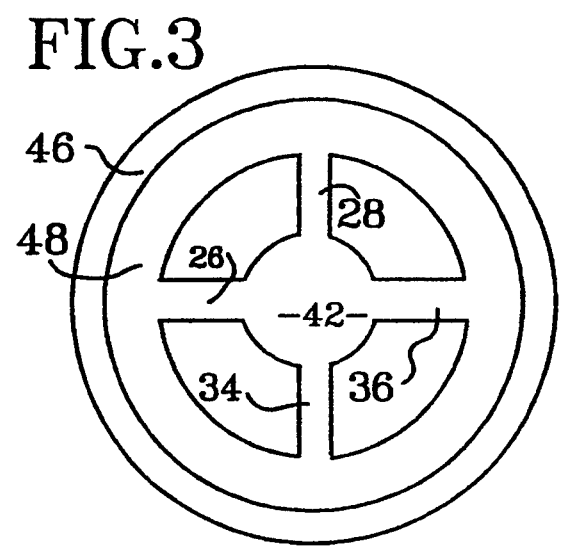
FIG. 3 is a top view of the closure cap of the instant invention.
Figure 2:
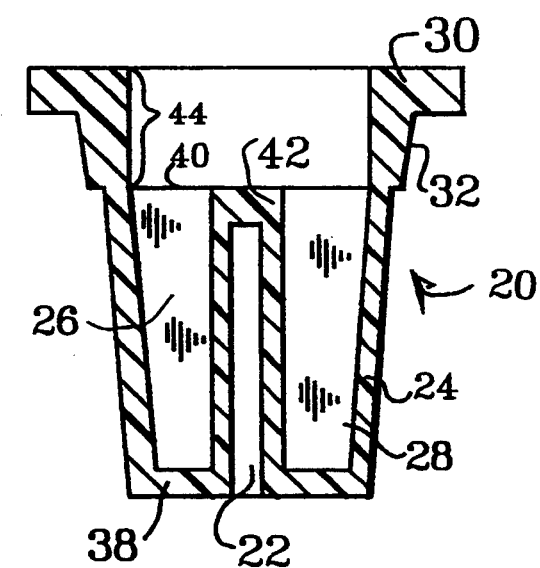
FIG. 2 is a cut away side view of the closure cap of FIG. 1.

A detailed illustration of the construction of the closure cap 20 is shown in FIGS. 2 and 3. The closure cap 20 is molded from a slightly flexible, inert material which can handle the temperatures and/or radiation required for sterilization. The preferred material of construction for the closure cap 20 is a synthetic rubber, or rubber like material such as EPDM, polychloroprene and chlorosulfonated polyethylene. The synthetic rubber sold under the trademark Santoprene ®, by Monsanto, provides the desired properties for the instant invention. Alcryn ® is a trademark of DuPont ® for a rubber which can be used. Other preferred materials include polyvinyl chloride homopolymers and copolymers, and thermoplastic polyurethane elastomers. The preferred method of manufacture is injection molding, although other methods can be employed if so desired. Although physically the closure cap 20 is a one-piece extruded unit, for purposes of description herein the closure cap 20 is divided into three areas, the gripping portion 30, the sealing portion 32 and the body exterior 24. In the preferred embodiment, illustrated herein in FIG. 2, the closure cap 20 is manufactured with the diameter, or periphery, being reduced twice from the original cap diameter, or gripping portion 30, to form a slightly truncated cone. The gripping portion 30 is dimensioned to be at least equal to, and preferably greater than, the diameter of the shipping tube 14. The overlap of the top of the shipping tube 14 prevents the closure cap 20 from being pushed down into the shipping tube 14. The gripping portion 30 also provides means to easily insert and remove the closure cap 20 from the shipping tube 14. The diameter of the gripping portion 30 is approximately 1.59 mm, thereby providing a diameter slightly greater than the 12×75 test tube. The slight flexibility of the material of manufacture allows the user to slightly squeeze the gripping portion 30 during removal, thereby allowing the air seal to be broken and the closure cap 20 to be easily removed from the shipping tube 14. The sealing portion 32 of the closure cap 20 is stepped down from the 1.59 mm diameter of the gripping portion 30 to approximately 1.07 mm to allow the sealing portion 32 to form a friction fit within the 12×75 shipping tube 14. The sealing portion 32 must be dimensioned to provide a firm friction fit within the shipping tube 14, however it must not be so difficult to insert or remove as to break or crack the shipping tube 14. The diameter of the body exterior 24 of the closure cap 20 is stepped down slightly, to 0.99 mm from the diameter of the sealing portion 32. The body exterior 24 further narrows very slightly as it extends to the body base 38. The body base 38 is molded with a 1.0076 mm micropipet receiving area 22, centered and extending into the micropipet retaining portion 42. It is critical that the micropipet receiving area 22 be dimensioned to exactly fit the exterior diameter of the micropipet 12. The fit must be an exact friction fit dimensioned to allow the insertion and removal of the micropipet 12, without cracking or breaking, while still holding the micropipet 12 rigid within the closure cap 20. The ability of the closure cap 20 to hold the micropipet firmly during transportation while allowing for safe insertion and removal is not just a matter of dimensioning the micropipet receiving area 22 for a friction fit. The micropipet receiving area 22 itself must be held firmly within the body exterior 24 of the closure cap 20 while retaining the ability to absorb impact. To accomplish this, the body exterior 24 is molded in a specific pattern which incorporates voids, or open areas, in combination with the material of manufacture.

The micropipet retaining portion 42 is retained in the center of the body exterior 24 through use of retaining bars 26, 28, 34 and 36. The retaining bars 26, 28, 34 and 36 extend from the base 38 of the body exterior 24 to the receiving edge 40. The upper wall 44 extending from the receiving edge 40 to the top of the closure cap 20 is maintained as an open area. The open area created by upper wall 44 allows the closure cap 20 to flex, or give, when the gripping portion 30 is engaged by the user. The retaining bars 26, 28, 34 and 36 prevent any extreme lateral movement of the micropipet 12 while serving to flexibly hold the micropipet retaining portion 42 in its proper position. The retaining bars 26, 28, 34 and 36 provide the critical locking of the micropipet retaining portion 42 in a position parallel to the walls of the shipping tube 14. As described further herein, a solid body provides too rigid a device. No support allows the micropipet retaining portion 42 to swing, thereby causing the ends of the micropipet to break against the shipping tube 14.

While preventing the micropipet 12 from swinging the extent of coming into contact with the sides of the shipping tube 14, the retaining bars 26, 28, 34 and 36 must allow for sufficient swing for shock absorption. The flexibility of the material of manufacture, in combination with the width of the retaining bars 26, 28, 34 and 36 allows the micropipet some movement upon impact. Total prevention of movement would, at sufficient impact, cause the micropipet to shear off at the base 38 of the body exterior 24. The shearing would be caused by the portion of the micropipet 12 within the micropipet retaining portion 22 coming in contact with a body of highly elastic material. The higher the elastic potential of a material, the greater the force it can withstand before reaching its elastic limit, or permanent deformity. Therefore the density of the elastic material of the closure cap would prevent any substantial movement of the portion of the micropipet confined within the cap. The remaining portion of the pipet 12 would be in contact with only air which provides little resistance to movement. This would allow the exposed portion of the micropipet to continue to move with the force until it came in contact with an object which would stop the movement. In this instance this would be the shipping tube 14. In order for one portion of the pipet to move with the force and the remaining portion to stay stationary, the delicate micropipet would shear at the point where it exits the receiving area 22. In order to avoid the shearing, the elastic potential of the closure cap must be reduced. This can be accomplished by changing the material of manufacture or by changing the physical structure of the closure cap. The material of manufacture is difficult to change as the material must be air impermeable, inert, heat and radiation resistant and able to maintain its shape through repeated uses. Any material which has sufficient density to meet the foregoing requirement has a relatively higher elastic potential. The material which is being shipped must also be taken into account. The micropipets are extremely delicate glass tubes and a material with an elastic potential which would provide a protective holder for a 1 inch diameter solid glass rod would not provide protection for a hollow glass tube with a diameter of approximately 1.0 mm.

Taking the foregoing into account, the structural design of the closure cap was altered to reduce the elastic potential of the material of manufacture. The use of retaining bars lowers the elastic potential of the body and provides the elasticity required to absorb a portion of the force created during an impact. The elastic potential must be high enough to prevent the micropipet from swinging so wide as to hit the side of the shipping tube 14 while being low enough to absorb a portion of the force to prevent shear. The retaining bars 26, 28, 34 and 36 also provide the contact between the micropipet retaining area 42 and the body exterior 24. In order for the force of impact to spread throughout the closure cap 20 there must be a physical connection between the micropipet retaining area 42 and the body exterior 24. Where there is too much physical connection, the elastic limit is too high (too highly rigid). Where there is too little or no connection, the elastic limit is non-existent or too low. The retaining bars 26, 28, 34 and 36 must have sufficient width to absorb and transmit the impact to the body exterior 24 without suddenly stopping the motion.

The use of four retaining bars provides the optimum protection with the minimum amount of material, however the dimensions of the retaining bars can be altered and the number increased or decreased to obtain equal protection. Three retaining bars would be the minimum number to provide the required absorption would be three, however the width of the retaining bars would have to be increased slightly to equal to the four retaining bars of the preferred embodiment. Although the number of retaining bars can be increased, the elastic limit must be reduced to account for the additional material. In order to reduce the elastic limit, the obvious method would to reduce the width of the retaining bars or use a manufacturing material different than the remaining closure cap. Both of these increase the cost of manufacture, although they may be of value in some instances. Great care must be taken to keep all tolerances, include the elastic limit, within the proportions set forth herein. Too high an elastic limit, whether it is caused by a solid or a nearly solid body, will cause shearing problems as set forth further herein.

FIG. 4 illustrates the closure cap 140 without the retaining bars 26, 28, 34 and 36 of the disclosed device. The diameter of the micropipet receiving area 142 is too easily expanded without retaining bars to secure the micropipet retaining area 144. Because of the ability of the diameter of the micropipet receiving area 142 to expand, the micropipet is not securely held in position during shipment. The motion created by shipment allows the micropipet to either work completely free, or far enough out of the micropipet receiving area 144 for the tip to hit the side of the shipping tube and break. When the micropipet retaining area 144 is free to move within the closure cap 140, there is little transference of force from the motion created by impact from the micropipet retaining area 144 to the closure cap 140. As stated heretofore, without the physical connection between the micropipet retaining area 142 and the wall 146 of the closure cap 140, there is no physical contact through which to transfer the force of impact.

In an attempt to resolve the problem of the micropipet working free, the the micropipet receiving area 154 and micropipet retaining area 152 were lengthened. The illustration of FIG. 5 shows the micropipet receiving area 154 and micropipet retaining area 152 extended to the entire length of the closure cap 150. This design allowed the micropipet to sit deeper in the body of the closure cap 150 and eliminated the problem of the micropipet working free. Without support, however, the micropipet retaining area 152 was too long to maintain any rigidity and the pipettes were free to swing within the tube, thereby breaking the ends. This problem extended to the removal of the closure cap from the shipping tube. When gripping the cap as designed in FIG. 5, it was almost impossible to keep the pipet centered in the shipping tube. The design illustrated in FIG. 5 is extended to the maximum, however this problem occurs when the micropipet retaining area 152 is extended greater than approximately three fifths the length of the closure cap 150.

In FIG. 6 the body 166 is partially filled to eliminate the swing of the micropipet receiving area 164. As previously stated, a solid body, whether full or partial, creates a shearing problem. Additionally, the use of a solid body 166 holding the micropipet 12 rigidly prevents any play within the micropipet retaining portion 162 for insertion and removal of the micropipet 12. This problem arises whether the micropipet receiving area 164 extends the full length of the closure cap 160 or only a portion of the body 166. The rigid body increases the breakage of the micropipet 12 as the micropipet 12 must be inserted exactly in line with the micropipet receiving area. The difficulty in removing the micropipet 12 also increases with a rigid body. The rigid, or partially rigid, body makes the pipet too difficult to remove, causing breakage at the point of exit from the body. Additionally, the rigid body does not allow for tolerances inherent in injection molding. Whenever handling testing with a liquid substance, such as blood or sperm, there remains the possibility that some of the liquid will be on the outside of the micropipet. A rigid body prevents any play, as allowed by the design of the disclosed device, to "break free" the micropipet. The use of retaining bars 26, 28, 34 and 36 allows the user to squeeze the closure cap 20, thereby slightly deforming the interior of the micropipet receiving area 22. The slight deformation allows the micropipet 12 to be more easily removed.

An alternate to the closure cap 20 is illustrated in FIG. 7 with closure cap 170. The closure cap 170 is designed with the micropipet retaining area 172 and micropipet receiving area 174 cone shaped. The cone shape allows for easier initial insertion of the micropipet, which is guided along the micropipet retaining area 172 within the decreasing micropipet receiving area. The cone must be dimensioned to allow the micropipet to wedge in to a secure position. Additionally the entrance 16 must have a dimension sufficient to prevent the micropipet from any extreme swinging within the shipping tube. The cone shape of the closure cap 170 allows for a greater tolerance to the outer diameter of the pipet. The smaller the outer diameter, the further into the closure cap 170 it can be inserted. It is critical, however, that the cone width not vary too greatly to prevent the side to side swinging disclosed heretofore in FIG. 4. A gradual variation of approximately 10% over the length of micropipet retaining area 172 is recommended to obtain maximum force absorption.

In FIG. 8 the threaded closure cap 80 incorporates a threaded shell 82 which is specifically threaded to mate with a container having the proportion receiving threads. The threaded shell 82 is preferably manufactured from a more rigid material than the closure cap to prevent the threads from warping and to facilitate closing. The threaded shell 82 has an interior diameter equal to that of the outer diameter of the sealing portion 84. The threaded shell 82 is preferably permanently affixed to the sealing portion 84 to prevent slippage and ensure a tight closure. The threaded shell 82 can be extended to cover at least a portion of the body exterior 86. Although the addition of the threaded shell 82 to the disclosed closure cap avoids the expense of creating a second mold, the threaded portion can be incorporated into the closure cap. The closure cap 90 of FIG. 9 has been molded with the threaded portion 92 forming the exterior periphery of the sealing portion 94.

It should also be noted that although the figures incorporated herein illustrate a round closure cap, other configurations can be substituted, such as square, octagon, etc. The round configuration does provide advantages in ease of manufacture and dimensioning and is therefore the preferred embodiment.

Since other modifications and changes varied to fit particular operating requirements and environments will be apparent to those skilled in the art, the invention is not considered limited to the example chosen for the purposes of disclosure, and covers all changes and modifications which do not constitute departures from the true spirit and scope of this invention.

What is claimed is:

1. A closure cap for use in protecting a hollow tube, said closure cap comprising;
   a) a hollow body member, said hollow body member having an exterior wall, said exterior wall being dimensioned to fit within a container and having a closed first end and an open second end,
   b) a tube retaining portion, said retaining portion being an elongated member having a diameter less than said exterior wall of said hollow body member and being substantially centrally positioned within, and coaxial with, said hollow body member and extending at least a substantial portion of the length of said hollow body member, said tube retaining portion having:
      a centrally disposed channel for receiving and retaining a tube, said channel having an open end proximate said first end of said hollow body member,
   c) a plurality of radially extending retaining webs, said plurality of retaining webs extending from said tube retaining portion and connecting said tube retaining portion and said exterior wall along at least a portion of the length of said tube retaining portion, d) void areas, said void areas being within said hollow body member between said retaining webs, e) a cylindrical region proximate said second end, f) a conical region proximate said first end, wherein said void areas, in combination with said radially extending retaining webs, provide a cushioning effect for said hollow tube, allowing impact to be transferred from said tube retaining portion through said retaining webs to said exterior wall.

2. The closure cap of claim 1, further comprising a sealing means, said sealing means region means positioned between said first end and said second end and having a periphery slightly greater than that of the region of said exterior wall between said sealing means and said first end, a gripping portion, said gripping portion having a outer periphery greater than the outer periphery of said sealing means and being positioned between said sealing means and said second end.

3. The closure cap of claim 1, wherein said hollow body member is tapered inwardly from said sealing means to said first end.

4. The closure cap of claim 1, wherein,
said hollow body member has a cylindrical region proximate said second end and a conical region proximate said first end,
said body member and the tube retaining portion being substantially coaxial,
said webs radiate outwardly from said tube retaining portion to said body member and connect said tube retaining portion and said body member along at least a major portion of the length of said tube retaining portion.

5. The closure cap of claim 4, wherein said webs lie in a plane which is parallel to the axis of said tube retaining portion.

6. The closure cap of claim 1, wherein at least a portion of said exterior wall is a circular cylinder.

7. The closure cap of claim 1, wherein said plurality of retaining webs are equally spaced from one another within said hollow body.

8. The closure cap of claim 1, wherein said plurality of retaining webs are at least three, substantially equally spaced webs, and each of said webs connect with said tube retaining portion along at least a major portion of the length of said tube retaining portion.

9. The closure cap of claim 1 wherein said closure cap is air impermeable, flexible and formed of an inert material.

10. The closure cap of claim 1 wherein said material is heat and radiation resistant.

11. The closure cap of claim 2 wherein said sealing means further comprises first threading means, and second threading means within a container, said first threading means having an exterior periphery dimensioned to threadably mate with said second threading means.

12. A shipping container for use in shipping micropipets in a impact absorbing, sterile environment, comprising:

a) a shipping member, said shipping member being an elongated hollow member having an open end and a closed end, and b) a closure cap, said closure cap having;

i) a hollow body member, said hollow body member having a first end and a second end, ii) an exterior wall, said exterior wall being dimensioned to fit within a container and extending between said first end and said second end, iii) a tube retaining portion, said retaining portion being an elongated member substantially centrally positioned within said hollow body member and extending at least a substantial portion of the length of said hollow body member, said tube retaining portion having
a centrally disposed elongated channel for receiving and retaining a tube, said channel having an open end, said channel open end being proximate said hollow body member first end, iv) a plurality of radially extending retaining webs, said plurality of retaining webs connecting said tube retaining portion and said exterior wall, said closure cap being positioned in said shipping container with said hollow body member first end being within said shipping member and said hollow body member second end adjacent said open end of said shipping member.

13. The shipping container of claim 12, further comprising sealing means, said sealing means being positioned between said hollow body first end and second end and having a periphery slightly greater than that of the region of said exterior wall between said sealing means and said first end, the periphery of said sealing means being dimensioned relative to the interior dimension of the open end of said shipping member, such that said sealing means is in friction fit engagement with said shipping member, a gripping portion having a outer periphery greater than the outer periphery of sealing means and being positioned between said sealing means and said second end.

14. The shipping container of claim 13, wherein said closure cap is air impermeable, flexible and formed of an inert material, whereby an air tight seal is provided between the interior of said shipping container and the exterior of said closure cap.

15. The shipping container of claim 14, wherein said air tight seal is formed by air sealing means, said air sealing means in combination with said sealing means prevent air entering or exiting said shipping container.

16. The shipping container of claim 15 wherein said air sealing means forms said first end of said closure cap.

17. The shipping container of claim 13 wherein said sealing means region further comprises threading means and said shipping member further comprises threaded receiving means, said threading means having a threaded exterior periphery dimensioned to cooperatively interact with said threaded receiving means.

18. The shipping container of claim 12, wherein said hollow body member is tapered inwardly from said sealing means to said first end.

19. The shipping container of claim 12, wherein,
said hollow body member has a cylindrical region proximate said second end and a conical region proximate said first end, said conical region allowing for ease of insert of said closure cap into said shipping member, said body member and said tube retaining portion being substantially coaxial,
said webs radiate outwardly from said tube retaining portion to said body member and intersect with said tube retaining portion along at least a major portion of the length of said tube retaining portion.

20. The shipping container of claim 12, wherein said webs lie in a plane which is parallel to the axis of said tube retaining portion and, in combination, have sufficient rigidity to provide structural rigidity to at least a portion of said closure cap exterior wall.

21. The shipping container of claim 12, wherein at least a portion of said exterior wall is a circular cylinder.

22. The shipping container of claim 12, wherein said plurality of retaining webs are equally spaced from one another within said hollow body.

23. The shipping container of claim 12, wherein said plurality of retaining webs are at least three, substantially equally spaced webs.

24. The shipping container of claim 12, wherein said closure cap material is heat and radiation resistant.

25. The shipping container of claim 12, wherein the end of said centrally disposed elongated channel opposite said open end is closed.

26. The shipping container of claim 12, wherein said hollow body member has a region proximate said first end which is the shape of a truncated cone.

27. The shipping container of claim 12, wherein said retaining webs are planar members axially position between said tube retaining portion and said hollow body member.

28. The shipping container of claim 12 wherein said centrally disposed channel is dimensioned to form a friction fit with a micropipet.

29. The method of shipping a fragile, hollow cylindrical object within a protective unit, said protective unit having:
a) a container, said container having an open end and a closed end;
b) a closure cap, said closure cap having
a first end,
a second end and
a hollow body member, said hollow body member having a first end and a second end,
an exterior wall being dimensioned to fit within a container and being extending between said first end and said second end,
a tube retaining portion, said tube retaining portion being an elongated member substantially centrally positioned within said hollow body member and extending at least a substantial portion of the length of said hollow body member, said tube retaining portion having,
a centrally disposed channel for receiving and retaining a tube, said channel having at least one open end proximate said first end,
a plurality of radially extending retaining webs, said plurality of retaining webs connecting said tube retaining portion and said exterior
a sealing portion, said sealing portion having a periphery slightly greater than that of said body portion to be in friction fit contact with the interior of said container,
a gripping portion, said gripping portion having a outer periphery greater than the outer periphery of said container, comprising the steps of:
inserting said fragile, hollow cylindrical object into said centrally disposed channel of said tube retaining portion through said open end,
inserting said closure cap containing said fragile, hollow cylindrical object into said container until said gripping portion is in contact with the edge of said shipping container,
whereby,
said sealing portion secures said closure cap within said container, and
said plurality of retaining webs resiliently maintaining said hollow cylinder centrally within the walls of said container.

* * * * *